US010179112B2

(12) United States Patent
Lu et al.

(10) Patent No.: US 10,179,112 B2
(45) Date of Patent: Jan. 15, 2019

(54) VIRAL VECTOR NANOCAPSULE FOR TARGETING GENE THERAPY AND ITS PREPARATION

(71) Applicants: THE REGENTS OF THE UNIVERSITY OF CALIFORNIA, Oakland, CA (US); Yunfeng Lu, Culver City, CA (US); Ming Yan, Los Angeles, CA (US); Irvin S. Y. Chen, Palos Verdes Estates, CA (US); Min Liang, Los Angeles, CA (US)

(72) Inventors: Yunfeng Lu, Culver City, CA (US); Ming Yan, Los Angeles, CA (US); Irvin S. Y. Chen, Palos Verdes Estates, CA (US); Min Liang, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/651,945

(22) PCT Filed: Dec. 16, 2013

(86) PCT No.: PCT/US2013/075362
§ 371 (c)(1),
(2) Date: Jun. 12, 2015

(87) PCT Pub. No.: WO2014/093966
PCT Pub. Date: Jun. 19, 2014

(65) Prior Publication Data
US 2015/0320693 A1 Nov. 12, 2015

Related U.S. Application Data

(60) Provisional application No. 61/737,233, filed on Dec. 14, 2012.

(51) Int. Cl.

| | |
|---|---|
| *A61K 9/51* | (2006.01) |
| *A61K 35/76* | (2015.01) |
| *A61K 48/00* | (2006.01) |
| *C12N 15/86* | (2006.01) |
| *A61K 31/7088* | (2006.01) |
| *A61K 47/62* | (2017.01) |
| *A61K 47/69* | (2017.01) |

(52) U.S. Cl.

CPC ............ *A61K 9/513* (2013.01); *A61K 9/5192* (2013.01); *A61K 31/7088* (2013.01); *A61K 47/62* (2017.08); *A61K 47/6925* (2017.08); *C12N 15/86* (2013.01); *A61K 9/5184* (2013.01); *C12N 2740/15045* (2013.01); *C12N 2760/20245* (2013.01); *C12N 2810/80* (2013.01); *C12N 2810/859* (2013.01)

(58) Field of Classification Search
None
See application file for complete search history.

(56) References Cited

U.S. PATENT DOCUMENTS

| | | | | |
|---|---|---|---|---|
| 4,450,153 | A | 5/1984 | Hopkins | |
| 7,279,318 | B1 * | 10/2007 | Seymour | A61K 47/6901 435/235.1 |
| 2007/0009441 | A1 | 1/2007 | Erathodiyil et al. | |
| 2008/0213869 | A1 * | 9/2008 | Mori | C12N 5/06 435/261 |
| 2008/0248126 | A1 | 10/2008 | Cheng et al. | |
| 2008/0312134 | A1 | 12/2008 | Hirt et al. | |
| 2009/0060894 | A1 | 3/2009 | Somberg et al. | |
| 2010/0297168 | A1 | 11/2010 | Charneau et al. | |
| 2011/0274682 | A1 * | 11/2011 | Tang | A61K 9/5138 424/94.63 |
| 2012/0107394 | A1 * | 5/2012 | Stover | A61K 9/0024 424/451 |

(Continued)

FOREIGN PATENT DOCUMENTS

| | | |
|---|---|---|
| WO | 2006-129080 | 12/2006 |
| WO | 2009-115579 | 9/2009 |

(Continued)

OTHER PUBLICATIONS

Ogawara et al., A Novel Strategy to Modify Adenovirus Tropism and Enhance Transgene Delivery to Activated Vascular Endothelial Cells In Vitro and In Vivo. Human Gene Therapy 15:433-443 (May 2004).*
Boudreau et al., Recombinant Vesicular Stomatitis Virus Transduction of Dendritic Cells Enhances Their Ability to Prime Innate and Adaptive Antitumor Immunity. Molecular Therapy, 2009, vol. 17 No. 8, 1465-1472.*
Croyle et al., PEGylation of a Vesicular Stomatitis Virus G Pseudotyped Lentivirus Vector Prevents Inactivation in Serum. Journal of Virology, Jan. 2004, p. 912-921 vol. 78, No. 2.*
Song et al., Preparation and characterization of hydrophobically modified polyacrylamide hydrogels by grafting glycidyl methacrylate. J Mater Sci (2007) 42:2775-2781.*

(Continued)

*Primary Examiner* — Christopher M Babic
*Assistant Examiner* — Arthur S Leonard
(74) *Attorney, Agent, or Firm* — Gates & Cooper LLP

(57) ABSTRACT

The invention provides novel methods, materials and systems that can be used to generate viral vectors having altered tissue and cell targeting abilities. In illustrative embodiments of the invention, the specificity of lentiviral vectors was modulated by a thin polymer shell that synthesized and coupled to the viral envelope in situ. The polymer shell can confers such vectors with new targeting ability via agents such as cyclic RGD (cRGD) peptides that are coupled to the polymer shell. These polymer encapsulated viral vectors exhibit a number of highly desirable characteristics including a higher thermal stability, resistance to serum inactivation in vivo, and an ability to infect dividing and non-dividing cells with high efficiencies.

17 Claims, 12 Drawing Sheets

(56) References Cited

U.S. PATENT DOCUMENTS

Figure 1:
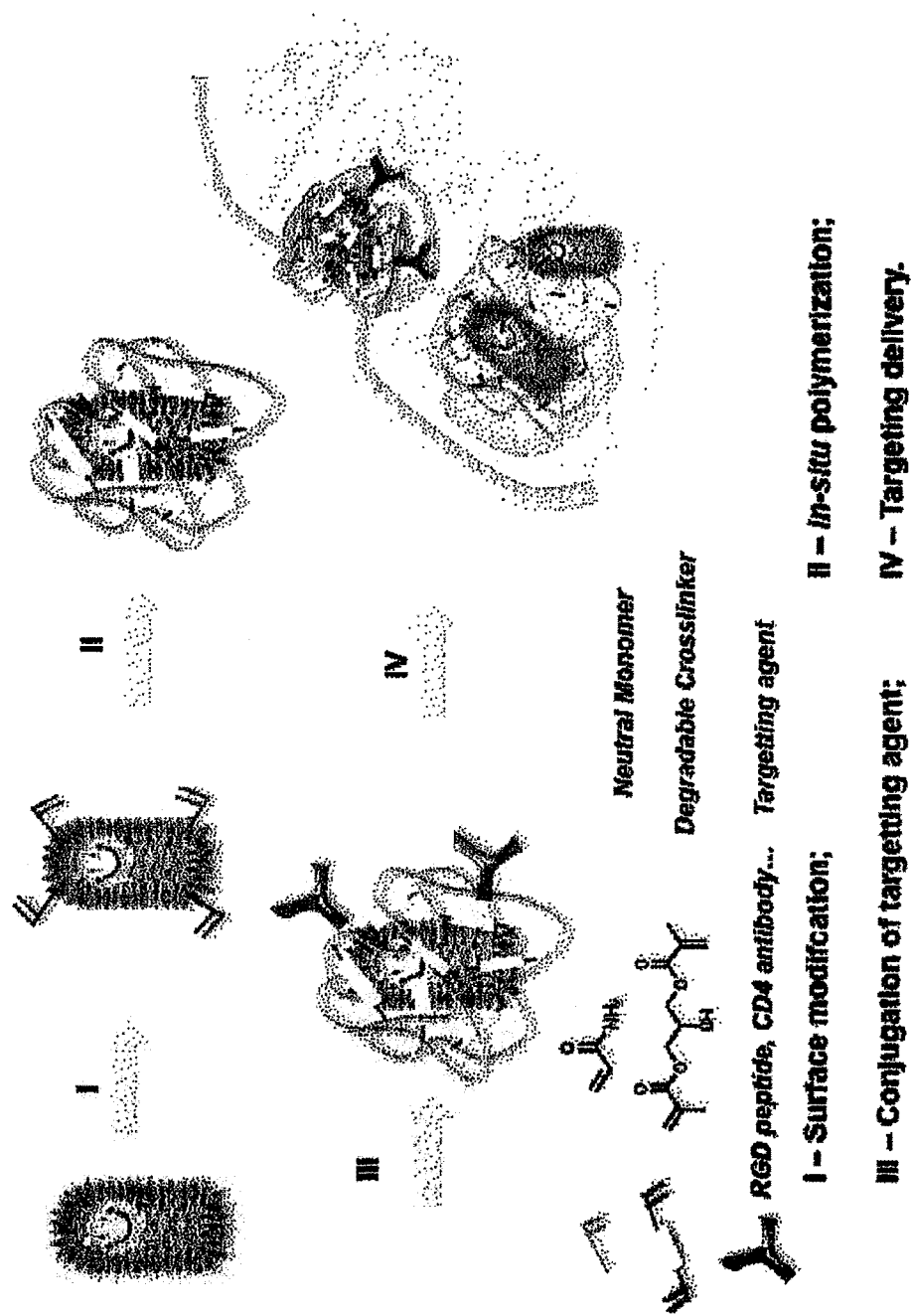

2014/0134700 A1    5/2014    Lu et al.
2015/0359752 A1    12/2015    Lu et al.

FOREIGN PATENT DOCUMENTS

WO    WO 2010/067041    *    6/2010
WO    2013138783            9/2013

OTHER PUBLICATIONS

You et al., Bioresponsive matrices in drug delivery. Journal of Biological Engineering 2010, 4:1-12.*

Bachtarzi et al, Targeting adenovirus gene delivery to activated tumour-associated vasculature via endothelial selectins. Journal of Controlled Release 150 (2011) 196-203.*

Yan et al., A novel intracellular protein delivery platform based on single-protein nanocapsules. Nature Nanotech, 2010, 5:48-53 (Year: 2010).*

Jang, Jae-Hyung et al. "Engineering biomaterial systems to enhance viral vector gene delivery", Molecular Therapy, vol. 19, No. 8, pp. 1407-1415, 2011.

Matsumoto, Hiroshi et al. "Effective in vivo and ex vivo gene transfer to intestinal mucosa by VSV-G-pseudotyped lentiviral vectors", BMC Gastroenterology, vol. 10, pp. 1-10, 2010.

Zhang, Xian-Yang et al. "Transduction of Bone-Marrow-Derived Mesenchymal Stem Cells by Using Lentivirus Vectors Pseudotyped with Modified RD114 Envelope Glycoproteins", Journal of Virology, vol. 78, No. 3, pp. 1219-1229, 2004.

PCT International Search Report and Written Opinion dated Apr. 21, 2014 from PCT/US2013/075362.

Jaesung Kim et al., "Active targeting of RGD-conjugated bioreducible polymer for delivery of oncolytic adenovirus expressing shRNA agains IL-8 mRNA", Biomaterials, Elsevier Science Publishers BV., Barking, GB, vol. 32, No. 22, Mar. 31, 2011, pp. 5158-5166, XP028214648, ISSN: 0142-9612, DOI: 10.1016/J. BIOMATERIALS. 2011.03.084.

Kim et al., "Active-targeting of RGD-conjugated bioreducible polymer for delivery of oncolytic adenovirus expressing shRNA against IL-8 mRNA". Biomaterials 32 (2011) pp. 5158-5166.

* cited by examiner

| | Relative transduction efficiency (%) |
|---|---|
| VSVG | |
| No block | 100 |
| cRGD peptide | 96 |
| cRAD peptide | 92 |
| Anti-integrins | 101 |
| Isotype control | 98 |
| cRGD-nVSVG | |
| No block | 100 |
| cRGD peptide | 40 |
| cRAD peptide | 97 |
| Anti-integrins | 70 |
| Isotype control | 96 |

FIG. 9

VIRAL VECTOR NANOCAPSULE FOR TARGETING GENE THERAPY AND ITS PREPARATION

CROSS-REFERENCE TO RELATED APPLICATIONS

This application claims the benefit under 35 U.S.C. Section 119(e) of U.S. Provisional Patent Application Ser. No. 61/737,233, titled "VIRAL VECTOR NANOCAPSULE FOR TARGETING GENE THERAPY AND ITS PREPARATION," filed Dec. 14, 2012, the contents of which are incorporated herein by reference.

STATEMENT AS TO RIGHTS TO INVENTIONS MADE UNDER FEDERALLY SPONSORED RESEARCH AND DEVELOPMENT

This invention was made with Government support under Grant No. AI069350, awarded by the National Institutes of Health, and Grant No. HDTRA1-09-1-0001, awarded by the U.S. Department of Defense, Defense Threat Reduction Agency. The Government has certain rights in this invention.

BACKGROUND OF THE INVENTION

Targeted gene transduction to specific tissues and organs is a desirable method of gene delivery. There have been many attempts to develop targeted gene transduction systems based upon various viral vectors. Adenovirus and adeno-associated virus vectors have been used in targeted gene delivery strategies because of their simple binding and entry mechanisms (see, e.g. Nicklin, et al. Curr. Gene Ther. 2, 273-293, 2002). Although these vectors have been used successfully in vitro for targeting to specific cells, their usefulness in vivo has been limited by their natural tropism (see, e.g. Muller, et al. Nat. Biotechnol. 21, 1040-1046, 2003), especially to liver cells (see, e.g. Martin, et al. Mol. Ther. 8, 485-494, 2003).

The application of specific targeting with retroviral vectors has also been problematic and the few studies of retroviral vector targeting in living animals are not efficient (see, e.g. Martin, et al. Mol. Ther. 5, 269-274, 2002; Jiang, et al. Gene Ther. 6, 1982-1987, 1999). Inserting ligands, peptides or single-chain antibodies into the retroviral receptor binding envelope subunit has been the most common approach used to alter or restrict the host range of retroviral vectors (see, e.g. Martin, et al. Mol. Ther. 5, 269-274, 2002; Jiang, et al. Gene Ther. 6, 1982-1987, 1999; Han, et al. Proc. Natl. Acad. Sci. USA 92, 9747-9751, 1995; Marin, et al. J. Virol. 70, 2957-2962, 1996; Nilson, et al. Gene Ther. 3, 280-286, 1996; Somia, et al. Proc. Natl. Acad. Sci. USA 92, 7570-7574, 1995; Valsesia-Wittman, et al. J. Virol. 68,4609-4619, 1994). Another approach is bridging virus vector and cells by antibodies or ligands (see, e.g. Boerger, et al. Proc. Natl. Acad. Sci. USA 96, 9867-9872, 1999; Roux, et al. Proc. Natl. Acad. Sci. USA 86, 9079-9083, 1989). In general, most strategies have suffered from inconsistent specificity and low viral titers as a result of modification of the retroviral envelope (see, e.g. Han, et al. Proc. Natl. Acad. Sci. USA 92, 9747-9751, 1995; Marin, et al. J. Virol. 70, 2957-2962, 1996; Nilson, et al. Gene Ther. 3, 280-286, 1996; Somia, et al. Proc. Natl. Acad. Sci. USA 92, 7570-7574, 1995; Valsesia-Wittman, et al. J. Virol. 68,4609-4619, 1994; Kasahara, et al. Science 266, 1373-1376, 1994).

Chemical modification of the Adenovirus vector with synthetic polymers such as polyethylene glycol (PEG) significantly reduce innate immune responses to the Adenovirus vector, evading pre-existing anti-Ad antibodies (see, e.g. Kreppel, et al. The American Style of Gene Ther. 16, 16-29, 2008). However in vivo targeting efficiency using PEGlated Adenovirus vector is still not sufficient and background infectivity still exists in liver cells (see, e.g. Lanciotti, et al. Mol. Ther. 8, 99-107, 2003). Although PEGlated VSV-G pseudotyped lentiviral vector was reported to be prevented from serum inactivation (see, e.g. Croyle, et al. J.V. 78, 912-921, 2004), targeting lentiviral vector by chemical modification has never been reported before.

The use of viral vectors having controllable targeting abilities has important implications for the use of such vectors in the clinic. For this reason, new methods and materials that can increase or modulate such targeting of cells or tissues are highly desirable.

SUMMARY OF THE INVENTION

The ability to introduce transgenes with precise specificity to target cells or tissues is key to a more facile application of genetic therapy. The invention disclosed herein provides novel methods, materials and systems that utilize nanotechnological techniques to generate viral vectors with altered recognition of host cell receptor specificity. In the working embodiments of the invention that are disclosed herein, the infectivity of the VSV-G envelope glycoprotein pseudotyped lentiviral vectors was shielded by a thin polymer shell synthesized in situ onto the viral envelope and new binding ability was conferred to the shielded virus by conjugating cyclic RGD (cRGD) peptide onto the polymer shell. These polymer encapsulated viral vectors are further shown to have a number of additional characteristics that are highly desirable including a higher stability at room temperature, resistance to serum inactivation in vivo, and an ability to infect dividing and non-dividing cells with high efficiencies.

Embodiments of the invention include, for example, a composition of matter comprising a viral vector encapsulated by a cross-linked degradable polymer shell to which one or more targeting agents is coupled. The targeting agents are typically polypeptides such as antibodies, receptors, ligands and peptides. For example, the targeting agent can comprise chimeric immunoglobulins, immunoglobulin chains or fragments thereof (such as Fv, Fab, Fab', F(ab')2 or other binding subsequences of antibodies). Targeting agents are typically selected to have a specific desirable affinity for a selected tissue, cell lineage, tumor cell or the like. In illustrative embodiments of the invention, the viral vector is a Vesicular stomatitis Indiana virus G protein (VSV-G) pseudotyped lentiviral vector, the cross-linked degradable polymer shell comprises at least one of N-acryloxysuccinimide (NAS), acrylamide or glycidyl methacrylate (GMA), and the targeting agent is a cyclic arginine-glycine-aspartic acid (cRGD), said cRGB having an affinity to an $\alpha_v\beta_3$ integrin on a tumor cell.

In one aspect of the present invention, chemical modification and in-situ polymerization is used to fabricate a cross-linked degradable polymer shell on the surface of a viral vector. This polymer shell functions to temporarily shield the native binding ability of the viral vector. Targeting agents are coupled to the surface of the polymer complex so as to direct the polymer encapsulated viral vector to specific cells such as tumor cells, neurons, and human mobilized PBMCs (see FIG. 1). These targeting agents then modulate vector targeting of specific cells or tissues Embodiments of the invention also include methods of preparing an encapsulated viral vector by reacting a polymerizable molecular anchor with a viral vector to generate a polymerizable group; reacting the polymerizable group to a plurality of monomers to form a polymer shell that encapsulates the viral vector; coupling the polymer shell with a degradable cross-linker; and further attaching a targeting agent to this complex. In some embodiments of the invention, the polymerizable molecular anchor is conjugated to a lysine of a protein expressed by the viral vector. In certain embodiment of the invention, the shell is formed from constituents (e.g. the degradable crosslinker) that degrade under certain condition, (e.g. an acidic environment), thereby releasing the viral vector from the polymer shell under those conditions. Optionally, for example the viral protein is a Vesicular stomatitis Indiana virus G protein (VSV-G) and the degradable cross-linker is glycidyl methacrylate (GMA). In some embodiments of the invention, the crosslinking agent is selected to comprise a peptide having an amino acid sequence that is cleaved by a protease. In certain embodiments, the targeting agent is a cyclic arginine-glycine-aspartic acid (cRGD), said cRGB having an affinity to an $\alpha_v\beta_3$ integrin on a tumor cell.

Other embodiments of the invention include methods for modulating the cellular specificity of viral vectors. Typically such methods comprise selecting a viral vector having a first specificity for a target tissue or cellular lineage and then encapsulating the viral vector in a shell formed from a plurality of polymers, polymers that are cross-linked by a degradable agent so as to form a polymer shell that can degrade in an in vivo environment. In such methods a targeting agent is further attached to the polymeric shell complex. This targeting agent is selected to have a second specificity for a target tissue or cellular lineage (e.g. a specificity for a cell lineage or tumor specific antigen). In this way, the cellular specificity of the viral vector can be modulated.

Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

BRIEF DESCRIPTION OF THE DRAWINGS

FIG. 1: Fabrication of viral vector nanocapsule.

FIG. 2: HeLa cell transduced by RGD conjugated VSVg-HIV lentiviral nanocapsules (Left: After; Right: Before).

FIG. 3: VSVg-HIV lentivirus Nanocapsules using RGD as targeting agent.

Different thickness and densities of the polymer result in different shielding of the viral infectivity. Best combination is NAS:virus=$2\times10^4$ with Monomers:virus=125.

FIG. 4: TEM pictures of VSVg-HIV lentiviral Nanocapsules (Left: VSVg-HIV; Middle:Nanocapsule (monomer to viral vector=125); Right: Nanocapsule (monomer to viral vector=250).

FIG. 5: Schematic illustration of the synthesis and delivery of VSV-G pseudotyped lentivirus nanocapsules: I) Surface modification of the lysine group of the envelope protein by NAS; II) In-situ polymerization of monomer and cross-linker at the surface of modified virus; III) Conjugation of the targeting agents onto the surface of the polymer shell; IV) Targeting delivery of the nanovirus to cells.

FIG. 6: Shielding of virus infectivity by polymer shell. 1×10^5 Hela cells were transduced with equal amount of VSVG, cRGD-nVSVG, and nVSVG (p24=10 ng). EGFP expression was monitored by flow cytometry.

FIG. 7: Optimization of transduction efficiency of the targeting nanovirus. VSV-G pseudotyped lentivirus (p24=60 ng) were reacted with different amounts of NAS and monomers with or without cRGD. P24=10 ng virus were then use to infect $1\times10^5$ Hela cells for 4 h. Virus transduction was monitored by EGFP expression 3 days after infection (Top panel). Sizes of the virus nanocapsules were measured by DLS (bottom panel). Left panel is virus with cRGD and right panel is virus without cRGD. At a combination ratio of NAS:virus (m/m=$2\times10^4$) and monomer:virus (w/w=125), we obtained the best transduction efficiency by cRGD-nVSVG (35%) while transduction efficiency by nVSVG is 0%. Transduction efficiency of VSV-G pseudotypes is 42%.

FIG. 8: Targeted transduction of Hela cells by the nanovirus is cRGD dependent. 1×10^5 Hela cells were transduced with equal amount of VSVG, cRGD-nVSVG, and cRAD-nVSVG (p24=10 ng) using the best ratio of NAS and monomer obtained from FIG. 7. EGFP expression was monitored by flow cytometry.

FIG. 9: Targeted transduction of Hela cells by the nanovirus is cRGD and integrin dependent. 1×10^5 Hela cells were pre-incubated with cRGD (1 mg/ml), cRAD(1 mg/ml), anti-integrins antibodies (20 ug/ml), and isotype control (40 ug/ml) for half and hour then transduced with equal amount of VSVG and cRGD-nVSVG (p24=10 ng).

FIG. 10: Entry kinetics of the targeting nanovirus by β-lactamase assay. Both VSV-G pseudotypes and targeting nanovirus incorporating the BlaM-Vpr fusion protein (p24=130 ng) were used to transduce 1×10^5 Hela cells for 5, 15, 30, 45, 60, 90, and 120 minutes. The percentage of cells with β-lactamase activity was measured by flow cytometry.

FIG. 11: Fusion and reverse transcription of the targeting nanovirus. A) 1×10^5 Hela cells were treated or not treated with vacuolar-type H+-ATPase inhibitor bafilomycin-A for half an hour then transduced with VSV-G or cRGD-nVSVG (p24=10 ng) with or without bafilomycin-A for 2 hour. B) Transduction by the nanovirus is inhibited by reverse transcriptase AZT. 1×10^5 Hela cells were treated or not treated with AZT for half an hour then transduced with VSV-G or cRGD-nVSVG (p24=10 ng) for 2 hour with or without AZT.

FIG. 12: Enhanced stability of the targeting nanovirus in the presence of human serum. VSVG or cRGD-nVSVG were pre-incubated with PBS, heat-inactivacted (HI) human serum (HS) or HS (v:v=1:1) for 1 h. The pre-treated virus (p24=10 ng) were then used to transduce 1×10^5 Hela cells.

DETAILED DESCRIPTION OF THE INVENTION

Unless otherwise defined, all terms of art, notations and other scientific terms or terminology used herein are intended to have the meanings commonly understood by those of skill in the art to which this invention pertains. Many of the techniques and procedures described or referenced herein are well understood and commonly employed using conventional methodology by those skilled in the art. All publications mentioned herein are incorporated herein by reference to disclose and describe the methods and/or materials in connection with which the publications are cited. Publications cited herein are cited for their disclosure prior to the filing date of the present application. Nothing herein is to be construed as an admission that the inventors are not entitled to antedate the publications by virtue of an earlier priority date or prior date of invention. Further the actual publication dates may be different from those shown and require independent verification. In the description of the preferred embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention.

Generally in this field of technology, chemical modification of viral vectors such as adenovirus vectors and VSV-G pseudotyped lentiviral vectors with synthetic polymers, such as polyethylene glycol (PEG), has used a "grafting-onto" strategy. This strategy includes two steps, activating linear polymers and conjugating polymers to the surface of the viral vector. However, the "grafting-onto" strategy can only conjugate linear polymers onto the viral surface, and thus the shielding of the viral infectivity is not complete. The invention disclosed herein provides methods, materials and systems that address such limitations in the art by utilizing polymer chemistry techniques to generate viral vectors having altered host cell specificities.

In one aspect of the present invention, a "growing-onto" process is provided to grow in-situ polymer networks on the surface of viral vectors with a controllable thickness and density, which provides better shielding of the native viral infectivity. Additionally, in one or more embodiments, the polymer shell is designed to be pH-sensitive and therefore can be removed in the endosome after endocytosis. This unshielding of the polymer from the viral vector within the endosome results in better infection activity. Furthermore, targeting efficiency is elevated by introducing as much targeting agents as possible to the surface of the virus nanocapsule.

In another aspect of the present invention, a method is provided for creating a virus nanocapsule with a highly controllable polymer shell for targeting gene therapy. This encapsulation approach provides the inner virus vector with a diversified targeting ability and extra stabilization upon serum inactivation.

Different monomers and cross-linkers may be used to encapsulate the viral vectors by conjugation and in-situ polymerization. Targeting agents, such as antibodies, peptides, or growth factors, are covalently conjugated with the polymer to allow for targeted gene transduction to specific tissues and organs through intravenous injection.

The invention provided herein combines the advantages of both viral vectors and polymer nanocapsules. The polymer encapsulated viral vectors provided have high stability at room temperature, can be prevented from serum inactivation in vivo, and can infect dividing and non-dividing cells with high efficiency. Chemical modification provides advantages over genetic modification (which is traditionally used in retargeting lentiviral and retroviral vectors) since the viral envelope is not disrupted by the mutation of amino acids and therefore the viral infectivity can be maintained after polymer encapsulation. Furthermore, chemical modification of the polymer to confer different properties (e.g. specificities, charges, stabilities to environment) is technically much easier than the genetic modification of virions. The diversified and controllable targeting ability provided to viral vectors by the nanocapsules may be used in clinical applications using viral vectors for targeting gene and protein delivery.

The invention disclosed herein has a number of embodiments. One embodiment of the invention is a composition of matter comprising a viral vector a degradable polymer shell encapsulating the viral vector. The viral vectors useful in the compositions and methods of the invention include retroviral vectors, adenoviral vectors, adeno-associated viral vectors, lentiviral vectors, herpes simplex viral vectors, vaccinia, pox viral vectors, and Sindbis viral vectors. As is known in the art, these retroviral vectors can exhibit variable tropism for different tissues (tissue tropism refers to the cells and tissues of a host which can be infected by, and typically support the growth of, a particular virus). In such compositions, a targeting agent can be selected and coupled to the encapsulated viral vector in order to direct the vector to certain cells or tissues (e.g. so that the cell or tissues targeted by the targeting agent are not those targeted by viral vector tropism). In typical compositions, the degradable polymer shell is crosslinked (e.g. with an agent such as glycerol dimethacrylate) and a targeting agent is coupled to the degradable polymer shell. In illustrative embodiments of the invention, the viral vector is a Vesicular stomatitis Indiana virus G protein (VSV-G) pseudotyped lentiviral vector.

In certain embodiments, the polymers that form the polymer shell are crosslinked by one or more degradable crosslinking compounds. Optionally, the crosslinker is a degradable crosslinker comprising a glycerol dimethacrylate, a N,N'-methylenebis(acrylamide), a 1,4-bis(acryloyl)piperazine, an ethylene glycol diacrylate, a N,N'-(1,2-dihydroxyethylene)bisacrylamide, or a poly(ethylene glycol)diacrylate (see, e.g. WO 2013/006762). In certain embodiments of the invention, the crosslinked polymeric network can be designed to exhibit a specific material profile, for example a surface charge of between 3 and 5 millivolts at a physiological pH.

In embodiments of the invention, the structure of the polymeric shell is designed in a manner that allows it to release the viral vector into selected environments. For example, in some embodiments of the invention, polymer components of the shell can be interconnected by disulfide-containing crosslinked moieties, linkages which maintain the integrity of the polymer shell under certain environmental conditions such as those typically found outside of cells (see, e.g. WO 2012/142410). Such linkages can be selected for an ability to degrade under other environmental conditions such as those that occur within the cellular cytosol. This degradation compromises the integrity of the polypeptide shell and results in the viral vector being released from this shell. As disclosed herein, by utilizing, for example, the redox potential differences that occur in different environments, a variety of viral vector delivery systems can be made. Embodiments of the invention include forming compositions of the invention by combining together a mixture comprising a viral vector, a plurality of polymerizable monomers; and a crosslinking agent selected for its ability to form disulfide bonds that are reduced in the cytosol of a mammalian cell. Illustrative embodiments of the invention include methods for using compositions of the invention for the intracellular delivery of viral vectors to cells or tissues not naturally infected by the virus.

In yet other embodiments of the invention, the crosslinking agent is selected to comprise a peptide having an amino acid sequence that is cleaved by a protease so that the polymer shell degrades in those in vivo environments where the protease is active (see, e.g. Biwas et al., ACS Nano. 2011 Feb. 22; 5(2):1385-94).

A number of targeting agents can be coupled to the polymer shells disclosed herein and used in the compositions and methods of the invention. For example, antibodies are known to be versatile tumor-targeting agents that can be used in embodiments of the invention (see, e.g. Lin et al., Clin Cancer Res (2005) 11; 129). In addition, a wide variety of ligands are useful as targeting agents can be adapted for use with embodiments of the invention (see .e.g. Brumlik et al., Expert Opin Drug Deliv. 2008 January; 5(1):87-103; Vaitilingam et al., J Nucl Med. 2012 July; 53(7):1127-34 and Das et al., Expert Opin Drug Deliv. 2009 March; 6(3):285-304). For example, ligands to P-selectin, endothelial selectin (E-selectin) and ICAM-1 have been found to adhere to inflamed endothelium (see, e.g. Barthel et al., Expert Opin Ther Targets. 2007 November; 11(11):1473-9). Certain embodiments of the invention can use cyclic arginine-glycine-aspartic acid (cRGD) molecules that are known to have an affinity to an $\alpha_v\beta_3$ integrin on tumor cells (see, e.g. Anderson et al., J Nucl Med 2010; 51:1 S-15S). In typical embodiments of the invention, the targeting agent binds a tumor cell, a neuronal cell or a peripheral blood mononuclear cell. For example, in illustrative embodiments of the invention, the targeting agent is a cyclic arginine-glycine-aspartic acid (cRGD), said cRGB having an affinity to an $\alpha_v\beta_3$ integrin on a tumor cell.

Methods of the invention include forming a mixture comprising a viral vector, a plurality of polymerizable monomers; and a crosslinking agent selected for its ability to degrade in certain in vivo environments (e.g. ability to form disulfide bonds that are reduced in certain in vivo environments). Optionally, the polymer shell degrades in an acidic environment (e.g. below about pH 6), thereby releasing the viral vector from the polymer shell. Alternatively, the polymer shell is designed to degrade in a basic environment (e.g. above about pH 8), thereby releasing the viral vector from the polymer shell. In typical embodiments of the invention the crosslinked polymer shell is designed to degrade in an acidic environment, thereby releasing the viral vector from the polymer shell. In illustrative embodiments of the invention, the crosslinked polymer shell can be adapted to remain stable at a pH of 7 and above (or a pH of 6 and above), yet degrade at a pH below 7 (or a pH of below 6, or a pH of below 5).

Optionally, the cross-linked degradable polymer shell comprises at least one of N-acryloxysuccinimide (NAS), acrylamide or glycidyl methacrylate (GMA). In such methods the mixture is exposed to conditions that first allow the plurality of polymerizable monomers and the crosslinking agent to adsorb to surfaces of the viral vector. Polymerization of the plurality of polymerizable monomers and the crosslinking agent at interfaces between the monomers and the viral vector is then initiated so that the modifiable polymeric nanocapsule is formed, one that surrounds and protects the viral vector. In certain embodiments of the invention, the plurality of polymerizable monomers comprises an acrylamide, the crosslinking agent comprises a cystamine moiety, and polymerization is initiated by adding a free radical initiator to the mixture.

Related embodiments of the invention include methods of preparing a viral vector encapsulated by a protective polymer shell. These methods can comprise reacting a polymerizable molecular anchor with a viral vector so as to generate a polymerizable group; and then reacting the polymerizable group to a plurality of monomers to form a polymer shell that encapsulates the viral vector. These methods can further comprise crosslinking the polymer shell with a degradable cross-linking agent. These methods can also comprise coupling a targeting agent (e.g. an antibody, a ligand or a growth factor) to the polymer shell. In common embodiments of the invention, the virus is selected to exhibit a specified tissue tropism, and for example, to bind a tumor cell, a neuronal cell or a peripheral blood mononuclear cell. In certain methods of the invention, the targeting agent is selected so that the cell or tissues targeted by the targeting agent are different those associated with the viral vector tropism. Optionally, the targeting agent is a cyclic arginine-glycine-aspartic acid (cRGD), said cRGB having an affinity to an $\alpha_v\beta_3$ integrin on a tumor cell.

Optionally in the methods, the polymerizable molecular anchor is coupled (e.g. covalently bonded to) to a lysine of a vector protein or a chemical group found on the polymer network. Commonly, one can react the polymerizable group to a plurality of monomers to form a polymer shell over a surface of the viral vector occurs in-situ. In illustrative embodiments of the invention, at least one viral protein expressed by the viral vector is a Vesicular stomatitis Indiana virus G protein (VSV-G), the polymerizable molecular anchor is N-acryloxysuccinimide (NAS), the monomer is acrylamide and/or the degradable cross-linker is glycidyl methacrylate (GMA). In typical embodiments of the invention, the m/m ratio of NAS to viral vector is between $0.5 \times 10^4$ and $5 \times 10^4$ (and preferably is $2 \times 10^4$) and the w/w ratio of monomer to virus is between 50 and 500 (and preferably is 125).

Other embodiments of the invention include methods of modulating the cellular specificity of a viral vector by temporarily masking the molecules that control viral tropism. Typically in these methods, one selects a viral vector having a first specificity or tropism for a target tissue or cellular lineage. In these methods, the viral vector is then encapsulated in a polymeric shell. This polymeric shell then temporarily masks the molecules found on the viral vector that control its tropism. In these methods, the shell then comprises a plurality of polymers that cross-linked by a crosslinking agent that is selected for its ability to degrade in one or more selected in vivo environments, so as to form a polymer shell that degrades in vivo. Additionally in these methods, a targeting agent can be attached to the cross-linked degradable polymer shell in a manner that allows the cell to target selected tissues and/or cells. In typical methods, the targeting agent is selected to have a specificity for a target tissue or cellular lineage that is different than that of the viral vector so that the cellular specificity of the viral vector is modulated.

EXAMPLES

A number of examples are provided as follows to illustrate the versatility and scope of embodiments of the instant invention.

Example 1: Viral Vector Nanocapsules for Targeting Gene Therapy and its Preparation We use chemical modification and in-situ polymerization to fabricate crosslinked degradable polymer shell on the surface of single viral vector with designed thickness and properties. This polymer shell shields the native binding ability of the viral vectors. Targeting agents, such as antibodies, peptides, or growth factors, are covalently conjugated on the surface of the polymer and direct targeting of the polymer encapsulated viral vectors to specific cells including tumor cells, neurons, and human mobilized PBMCs (FIG. 1).

Figure 2:
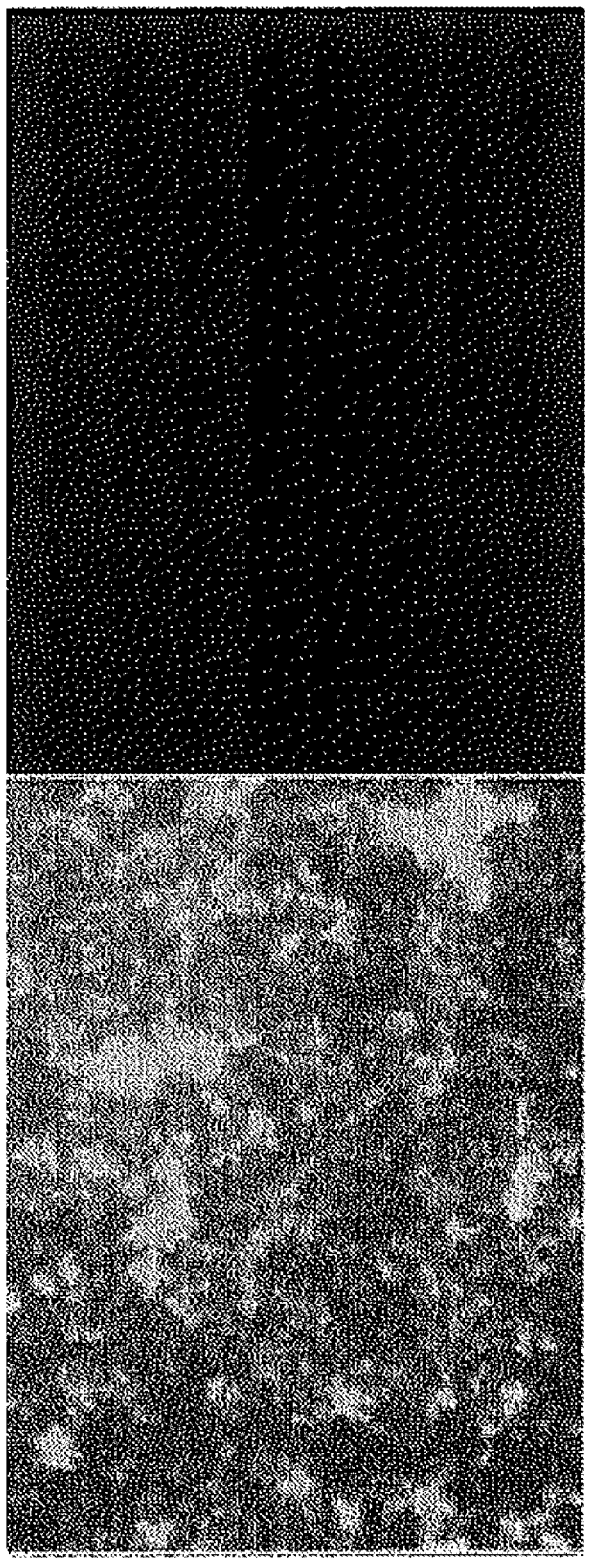
Figure 3:
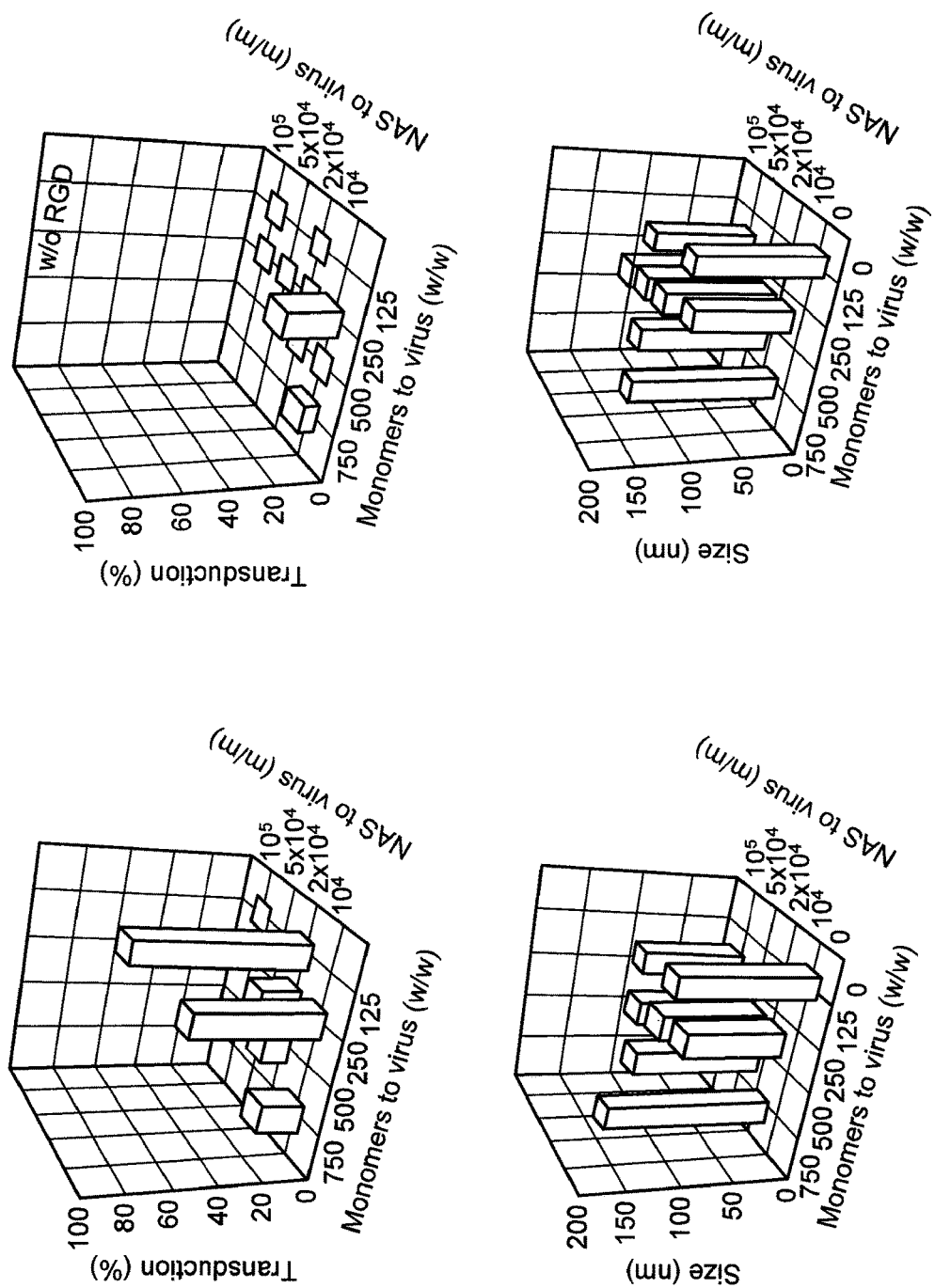

The transduction of Hela cells with RGD conjugated VSVg-HIV lentiviral nanocapsules is shown in FIG. 2. Transduction is indicated by the expression of EGFP in the cells. To test the effect of different thicknesses and densities of the polymer on viral transduction, the VSV-G pseudotyped lentiviral vectors were encapsulated with different concentrations of NAS and monomers. As shown in FIG. 3, an increased concentration of NAS and monomers results in better shielding of the native viral infectivity, however, overshielding of the viral vector could also result in decreased transduction efficiency of the RGD conjugated viral nanocapsules. Therefore, a balance of the shielding and targeting transduction efficiency is required in the design of nanocapsules.

Figure 4:
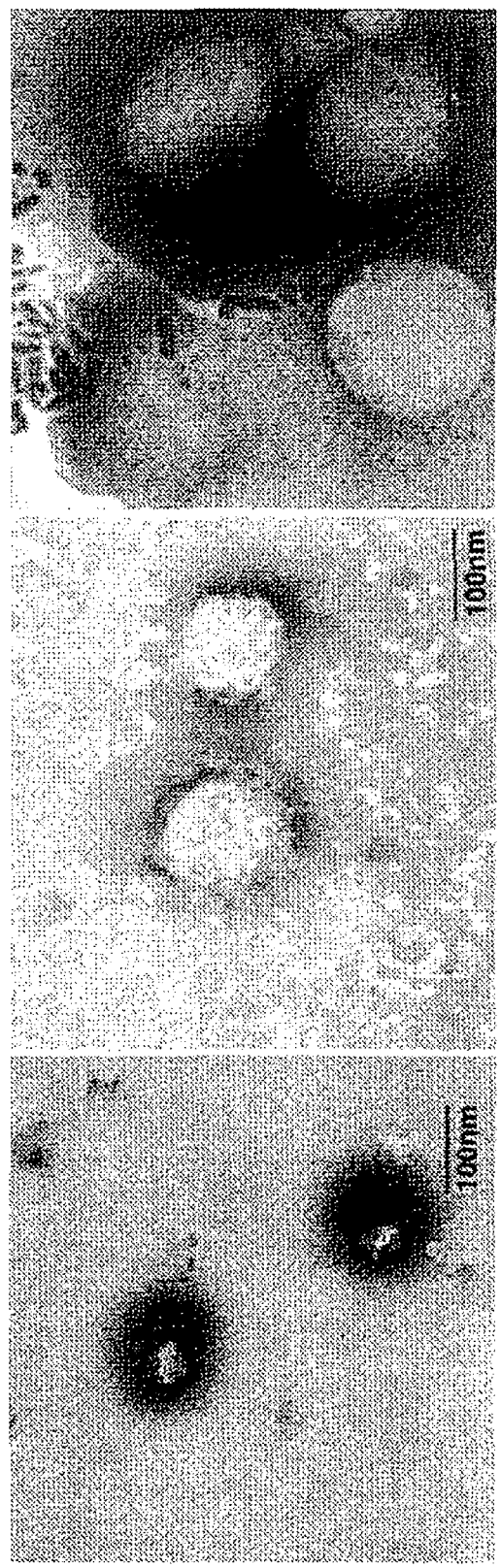
Figure 5:
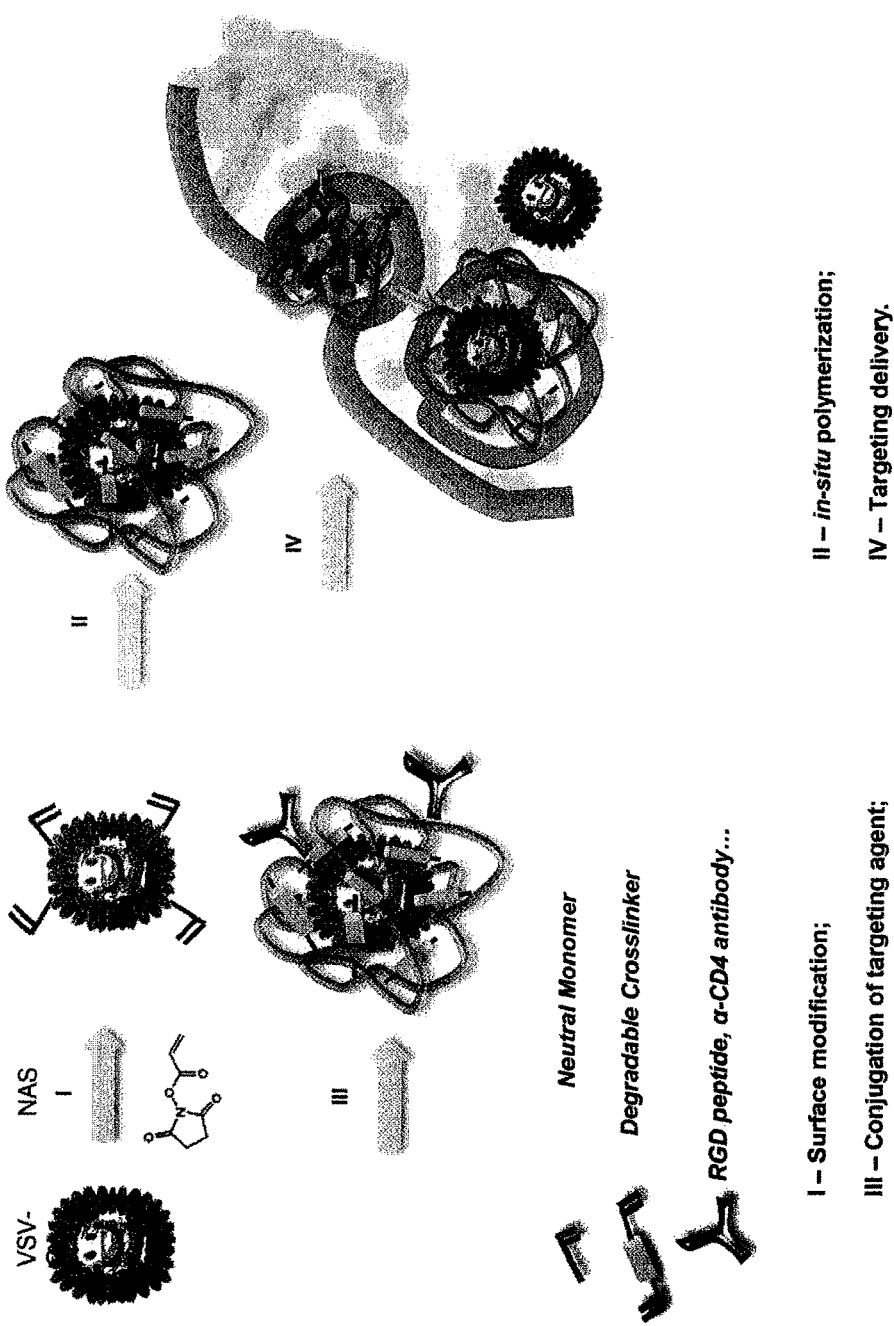
Figure 6:
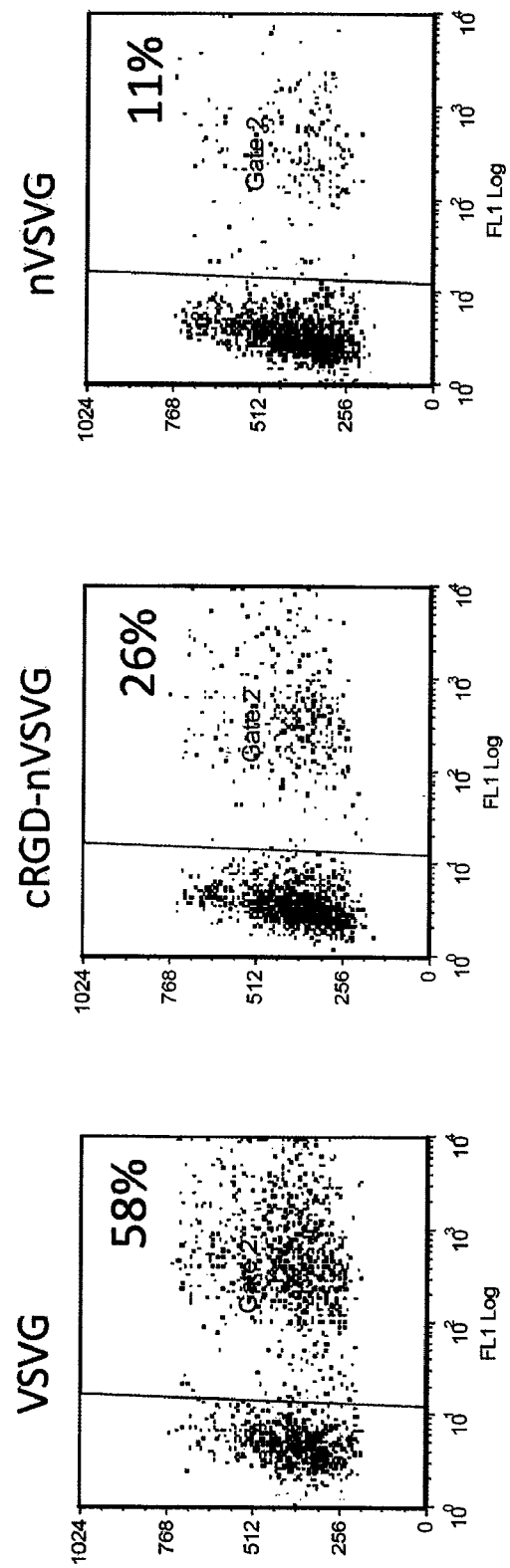
Figure 7:
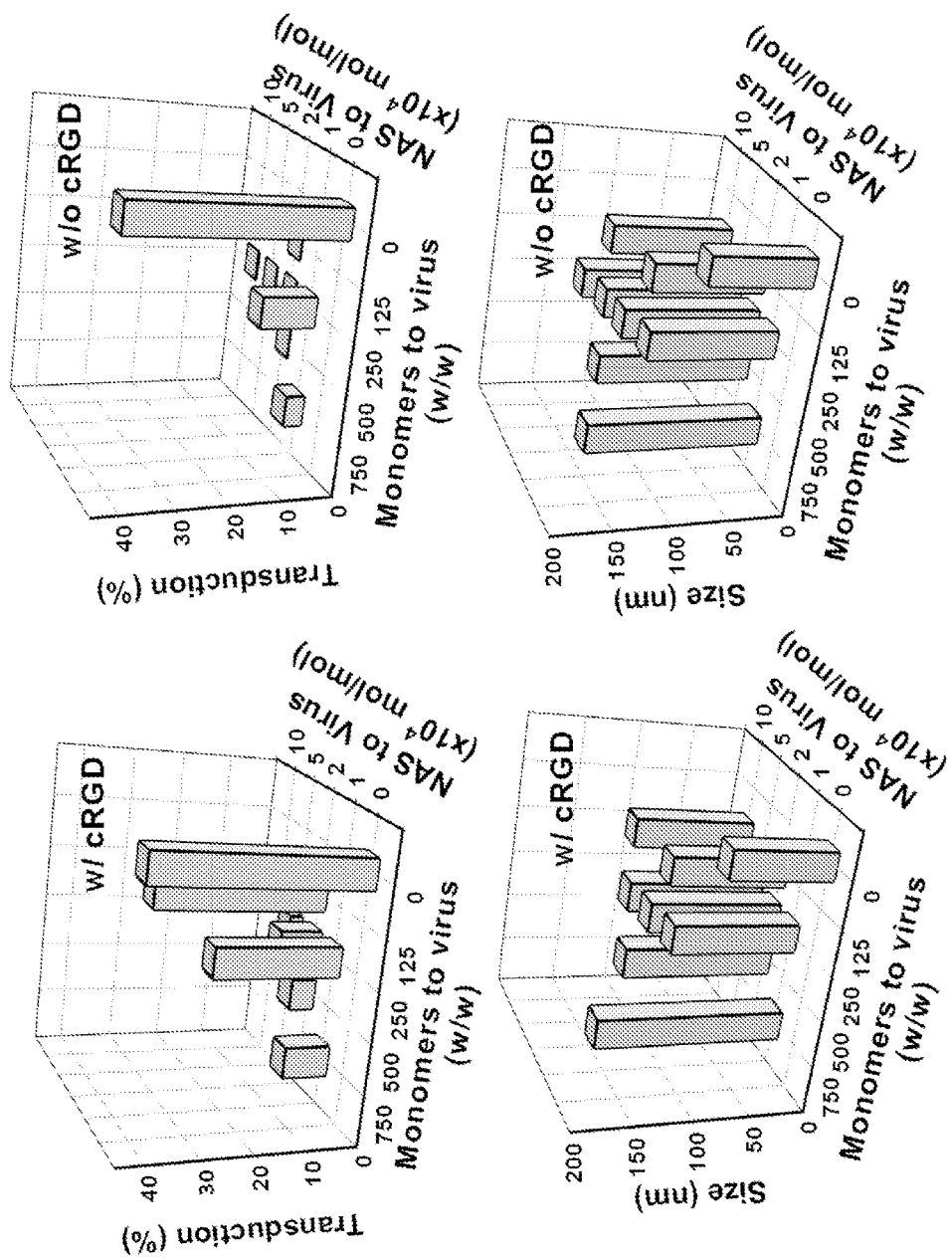
Figure 8:
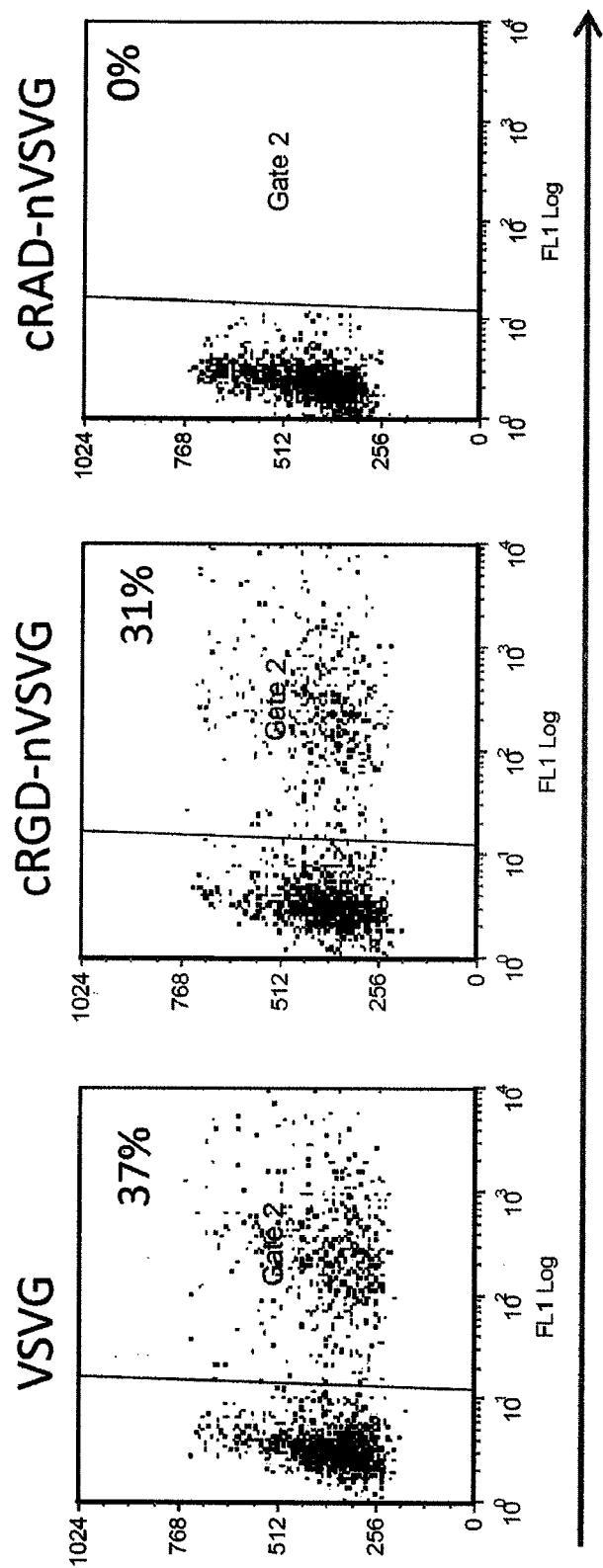

In our test, we found that a combination of NAS:virus ($2\times10^4$) and Monomer:virus (125) can completely shield the native viral infectivity without affecting the transduction efficiency by RGD conjugated viral nanocapsules (FIG. 3). We also studied the nano-structure of the viral nanocapsules via Transmission Electron Microscopy (TEM). Pictures of the native VSV-G pseudotyped lentiviral virus and VSVg-HIV lentiviral nanocapsules with different thicknesses are shown in FIG. 4. The thicker the polymer the bigger the nanocapsule.

Example 2: Retargeting VSV-G Pseudotyped Lentiviral Vectors with Enhanced Stability by In Situ Synthesized Polymer Shell The ability to introduce transgenes with precise specificity to the desired target cells or tissues is key to a more facile application of genetic therapy. Here, we describe a method using nanotechnology to generate lentiviral vectors with altered recognition of host cell receptor specificity. Briefly, the infectivity of the VSV-G pseudotyped lentiviral vectors was shielded by a thin polymer shell synthesized in situ onto the viral envelope and a new binding ability was conferred to the shielded virus by conjugating cyclic RGD (cRGD) peptide onto the polymer shell. We termed the resulting virus "targeting nanovirus". The targeting nanovirus has similar titer with VSV-G pesudotypes and specifically transduced Hela cells with high transduction efficiency. In addition, the encapsulation of the VSV-G pseudotyped lentivirus by the polymer shell did not change the pathway that VSV-G pseudotypes enter and fuse with cells as well as later events such as reverse transcription and gene expression. Furthermore, the targeting nanovirus possessed enhanced stability in the presence of human serum, indicating protection of the virus by the polymer shell from human serum complement inactivation. This novel use of nanotechnology demonstrates an approach which can be more generally applied for redirecting viral vectors for laboratory and clinical purposes.
Introduction Stably integrating retroviral and lentiviral vectors are commonly utilized for gene delivery (see, e.g. Aiuti et al. (2009) The New England Journal of Medicine 360, 447-458; Aiuti et al. (2002) Science 296, 2410-2413; Cartier et al. (2009) Science 326, 818-23; and Cavazzana-Calvo et al. (2000) Science 288, 669-672). Because the current vectors have broad host range, typically due to pseudotyping with VSV-G envelope (see, e.g. Marsh and Helenius (1989) Adv Virus Res 36, 107-51), the vectors are limited in their use to applications where the desired target cells and tissues can be purified and/or physically isolated for transduction. The creation of retroviral vectors which can target specific cells within mixed populations allows a more general application of genetic therapy. The primary obstacles have been modification of vector envelopes to specifically target while at the same time maintaining virion stability and titer (Han et al. (1995) Proc Natl. Acad Sci U.S.A. 92, 9747-9751; Kasahara et al. (1994) Science 266, 1373-1376; Marin et al. (1996) J. Virol. 70, 2957-2962; Nilson et al. (1996) Gene Therapy 3, 280-286; Somia et al. (1995) Proc Natl. Acad Sci U.S.A. 92, 7570-7574; Valsesia-Wittmann et al. (1994) J. Virol. 68, 4609-4619; Yu and Schaffer (2005) Adv Biochem Eng Biotechnol 99, 147-67). In addition, viral envelopes encode a variety of receptor binding moieties that are non-target cell specific, such as binding to heparin sulfate, laminin, integrins, carbohydrates, lipids, etc. (Haywood (1994) J Virol 68, 1-5).

Several retroviral systems have been reported to redirect vectors to specific cells; yet, few accomplish targeting while maintaining high titers of stable transduction (Han et al. (1995) Proc Natl. Acad Sci U.S.A. 92, 9747-9751; Kasahara et al. (1994) Science 266, 1373-1376; Valsesia-Wittmann et al. (1994) J. Virol. 68, 4609-4619). Modification of lentiviral vectors to achieve specific targeting requires two approaches. First, modifications to vectors must be made so that they can utilize unique cell surface molecules as new receptors to redirect vector binding to the desired target cells. We have successfully accomplished targeted transduction in vitro and in vivo using a modified Sindbis virus envelope pseudotype (Liang et al. (2009) Journal of Gene Medicine 11, 185-96; Morizono et al. (2001) Journal of Virology 75, 8016-8020; Morizono and Chen (2005) Cell Cycle 4, 854-6; Morizono et al. (2010) Journal of Virology 84, 6923-34; Morizono et al. (2009) Journal of Gene Medicine 11, 549-58; Morizono et al. (2006) Virology 10, 71-81; Morizono et al. (2005) Cell Cycle 4, 854-6; Pariente et al. (2008) Journal of Gene Medicine 10, 242-8; Pariente et al. (2007) Mol Ther. 15, 1973-1981). Our initial construct consisted of a Sindbis virus envelope pseudotype modified by conjugation with affinity reagents such as antibodies directed to cell surface molecules or genetically engineered for covalent incorporation of ligands that bind specific cell surface molecules. We demonstrated that our vectors could be utilized in murine models to target tumors (Morizono et al. (2005) Cell Cycle 4, 854-6; Pariente et al. (2007) Mol Ther. 15, 1973-1981). The second complementary approach is to reduce off-target binding. We made several specific mutations which ablate native receptor binding of the Sindbis envelope. However, a residual low-level, non-specific binding complicated the targeted transduction. We recently identified one source of non-specific binding mediated through virion phosphatidylserine binding to molecules which bridge to receptors on the cell surface (Morizono et al. (2011) Cell Host Microbe 9, 286-98).

In addition to genetic and metabolic modifications of the virus envelope for targeting, chemical modifications of viral vectors were also reported for adenovirus and VSV-G pseudotyped lentivirus. Until now, chemical modification of adenovirus vectors and VSV-G pseudotyped lentiviral vectors with synthetic polymers such as polyethylene glycol (PEG) uses a "grafting-onto" strategy. This strategy includes two steps, activating linear polymers and conjugating polymers to the surface of the viral vector. "Grafting-onto" strategy can only conjugate linear polymers onto the viral surface therefore the shielding of the viral infectivity is not complete. For example, modification of Adenovirus vector with PEG significantly reduces innate immune responses to Adenovirus vector, evades pre-existing anti-Ad antibodies (Giordano et al. (2011) Human Gene Therapy 22, 697-710; Lee et al. (2005) Biotechnol Bioeng 92, 24-34; Muller-Sieburg et al. (2004) Blood 103, 4111-8; Muller-Sieburg et al. (2012) Blood 119, 3900-7). However in vivo tageting efficiency using PEGlated Adenovirus vector is still not sufficient and background infectivity still exists in liver cells (Kreppel and Kochanek 2008). VSV-G envelope protein confers unobtainable robust physical stability on the virus-like particles which prevents it from being disrupted by shear forces encountered during concentration by ultracentrifugation and multiple freeze-thaw cycles. However, use of VSV-G pseudotyped vectors in vivo continues to be hampered by an innate immune response directed against the virus particles (DePolo et al. (2000) Mol Ther 2, 218-22). This effect is largely mediated through the classical complement pathway (Beebe and Cooper (1981) J Immunol 126, 1562-8). Although PEGlated VSV-G pseudotyped lentiviral vector was reported to be prevented from human serum complement inactivation (Croyle et al. (2004) J Virol 78, 912-21), chemical modification to redirect VSV-G pseudotyped lentiviral vectors to new receptors has not been previously reported.

We previously synthesized a family of small nanocapsules in which single protein molecules were encapsulated into an organic polymer nanocapsule with a thin crosslinked network shell (Yan et al. (2010) Nature Nanotechnology 5, 48-53; Yan et al. (2006) Journal of the American Chemical Society 128, 11008-9). Different from the "grafting-onto" strategy, the crosslinked network shell were synthesized on the protein surface by a two-step "growing-onto" process. First, A polymerizable molecular anchor, N-acryloxysuccinimide (NAS) was used to react with the lysine of the protein to generate polymerizable groups; II) These polymerizable groups then react with the vinyl groups of the monomers, such as acrylamide, to form polymers on the viral surface. Crosslinkers, such as Glycerol dimethacrylate (GMA), were included in the reaction to stabilize the polymer structure. These nanocapsules presented uniform size (~20 nm), high protein activity retention, and outstanding protein stability. Such nanocapsules exhibited two orders of magnitude higher efficiency of intracellular delivery compared with protein transduction through TAT peptide conjugation; moreover the polymer shell protects the proteins from protease attack and thermal inactivation, greatly increasing the half-life of the protein payload. The in vitro toxicity of nanocapsules was lower than those using TAT peptide conjugation. Recent studies also show success in delivery and low toxicity in vivo in mouse models. We also directed targeting delivery of EGFP nanocapsules to cells expressing CD4 by conjugating anti-CD4 antibodies onto the nanocapsules.

In this study, we applied this in situ polymerization method to encapsulate VSV-G pseudotyped lentivirus with crosslinked polymer shell and generated a targeting nanovirus with enhanced targeting ability, infectivity, and stability for gene therapy.

Materials and Methods

Virus Production and Titer

All lentivirus vectors were produced by calciumphosphate-mediated transient transfection of 293T cells, as previously described (Morizono et al. (2001) Journal of Virology 75, 8016-8020; Morizono and Chen (2005) Cell Cycle 4, 854-6). Briefly, 293T cells ($1.8\times10^7$ cells) were transfected with 12.5 μg of pCMVR8.2_VPR, 12.5 μg of SIN18-RhMLV-E with central polypurine tract (termed cppt2e) and 5 μg VSV-G expressing plasmids. 6 ug Beta lactamase-Vpr fused protein-coding plasmid was included for generating VSV-G psuedotyped virus packaging with beta lactamase. The viral vectors were harvested in AIM V® Medium (Invitrogen, Carlsbad, Calif., USA) with antibiotics. Lentiviral vectors were concentrated by ultracentrifugation at 28,000 RPM for 90 min at 4° C. by SW32 rotor (Beckman, Palo Alto, Calif., USA). The pellets were resuspended in a 100-fold lower volume of PBS. The viral titer was measured by anti-p24 Gag enzyme-linked immunosorbent assay (ELISA). Reporter gene expression was monitored by flow cytometry. Data were collected on a Cytomics FC500 (Beckman Coulter, Fullerton, Calif., USA) and analysed using FCS express (De Novo Software, Los Angeles, Calif., USA).

Synthesis of Acryl-cRGD

Cyclic [Arg-Gly-Asp-d-Phe-Lys(PEG-PEG)], which is marked as cRGD, was order from Peptides International, Inc. The preparation of acryl-cRGD was achieved by reacting cRGD with acrylic acid, hydroxysuccinimide ester (NAS). Briefly, cRGD (5 mg) was dissolved in 1 mL pH=8 50 mM HEPES buffer and NAS (1.2 mg) were dissolved in 100 uL DMSO. The NAS solution was then added into the cRGD solution gradually at room temperature. After overnight reaction, the mixture was diluted to 0.02% with 1×PBS buffer as stock.

Synthesis and Size Characterization of Nanovirus

100× concentrated VSV-G pseudotyped lentivirus were dialyzed in 1×PBS buffer at 4° C. overnight. The viral titer was measured by anti-p24 Gag ELISA. 5 mg N-acryloxysuccinimide (NAS) (Sigma #A8060) was dissolved in 0.1 mL of DMSO and diluted to 0.002% with ice-cold 1× PBS buffer. NAS solution was added to the virus (p24=60 ng) at different molar ratios (m/m) of 1×10^4, 2×10^4, 5×10^4, and 1×10^5. The reaction was carried out for 1 h at 4° C. 1 μL of 100 mM pH=7 TRIS buffer was added to the microtube to stop the surface modification by NAS. A cocktail solution containing 2% (w/v) acrylamide (Sigma #A3553), 2% (w/v) GMA (Sigma #436895), 0.5% (w/v) APS (Sigma #A3678) and 0.1% (w/v) N,N,N',N'-tetramethylethylenediamine (Sigma #T9281) were added to the NAS modified virus at different weight ratios (w/w) of 125, 250, 500, 750 with or without acryloxilated cRGD (0.02%) at a molar ratio of 2×10^4 to initiate the radical polymerization at the surface. The reaction was allowed to proceed at 4° C. for another 60 min. Size distribution of the virus and nanovirus (p24=60 ng) were measured by dynamic light scatter (DLS) with a Malvern particle sizer Nano-ZS in 1×PBS buffer.

Virus Transduction

Both VSV-G pseudotypes and targeting nanovirus (p24=10 ng) were used to transduce 1×10^5 Hela cells for 4 hours, then cells were washed twice with 1× PBS, cultured in 500 μl DMEM/10% FBS/1% GPS for 2 days. Reporter gene expression (EGFP) was monitored by flow cytometry. For blocking assay, cRGD (1 mg/ml), cRAD(1 mg/ml), a mixture of anti-integrin antibodies (20 μg/ml of both anti-integrin αVβ3 and αVβ5 antibody) (Chemicon), or isotype control antibody (40 μg/ml) were incubated with the virus 30 minute prior to and during the infection. For fusion assay, bafilomycin-A (Sigma, B1793) was incubated with the virus at a final concentration of 125 nM 30 minutes prior to and during the transduction. For reverse transcription assay, AZT (Sigma, A2169) was incubated with the virus at a final concentration of 25 μM during virus infection. Cells were washed with 1× PBS and continued cultured in the presence of AZT for 2 days before flow cytometry analysis.

Entry Assay

Both VSV-G pseudotypes and targeting nanovirus incorporating the Vpr-β-lactamase fusion protein (p24=130 ng)

were used to transduce 1×10^5 Hela cells for 5, 15, 30, 45, 60, 90, and 120 minutes. Cells were washed twice with 1× PBS. Beta lactamase substrate CCF2-AM (Invitrogen, K1039) was incubated with cells for 2 h at room temperature in dark following company protocol. Fluorescence was monitored by flow cytometry.

Results

Synthesis of Targeting Nanovirus

The virus envelope is comprised of proteins, lipids and carbohydrates. Since proteins are major components of the envelope, we considered our previous method of synthesis protein nanocapsules could be applied to synthesize virus nanocapsules. We hypothesize that the crosslinked polymer shell synthesized around the virion will ablate native infectivity of the virus and new target binding ability can be conferred through ligands conjugated on the surface of the polymer shell. To synthesize targeting virus nanocapsule, we used a three-step procedure to modify the VSV-G pseudotyped lentiviral vectors expressing EGFP (FIG. 5), I) A polymerizable molecular anchor, N-acryloxysuccinimide (NAS) was used to react with the lysine of the VSV-G envelope protein to generate polymerizable groups; II) These polymerizable groups then react with the vinyl groups of the monomers (acrylamide) to form polymers on the viral surface. Crosslinkers (GMA) were included in the reaction to stabilize the polymer structure. The crosslinkers are degradable at pH<6 which allows release of the virion from the polymer shell at an acidic environment such as endosome; III) New binding activity is then conferred by targeting molecules chemically-conjugated on the polymer shell via reaction with the excessive vinyl groups on polymers (Michael-addition reactions). To target Hela cells, we generated a targeting nanovirus conjugating with cyclic arginine-glycine-aspartic acid (cRGD), which displays a strong affinity and selectivity to the $\alpha_v\beta_3$ integrin and is abundantly expressed on tumor endothelial and tumor cells.

In the synthesis of both protein and virus nanocapsules, the polymerization process starts with reaction of polymerizable molecular anchors (NAS) with lysine of the protein or envelope protein of the virus. Although the mechanism of polymerization is similar, there are several differences to encapsulate a virus compared to a single protein. First, the size of virus (~100 nm) is bigger than a single protein (~10 nm). To fully encapsulate a virion, the amounts of NAS and monomers as well as the reaction time need to be adjusted. Second, virus is stable at 4° C. To maintain virus stability thus their infectivity, we optimized the reaction temperature to be 4° C. instead of 25° C. previously used for protein. Third, efficient polymerization requires high concentration of substrate. We concentrated the virus to achieve a high concentration of 100 μg/mL to accelerate the polymerization process.

Optimization of Transduction of cRGD Conjugated Targeting Nanovirus in Hela Cells Composition, size, and degradability of the polymer shell of the targeting nanovirus are the essential parameters affecting their delivery efficiency and potency. The amount of NAS determines the amount of surface anchor for subsequent polymerization thus the gap distance between the polymers. The amount of monomers controls the length of the polymer thus the size of the polymer shell. Increased concentration of NAS and monomers resulted in a better shielding of the native viral infectivity, however, overshielding of the viral vectors might also led to diminish transduction efficiency of the targeting nanovirus. Therefore, a balance of shielding and targeting transduction efficiency is required in the design of targeting nanovirus. We first tested a ratio of NAS:virion (m:m=1×10^4) with a ratio of monomer:virion (w:w=250) and achieved transduction efficiency of 26% with cRGD conjugation and 11% without cRGD conjugation compared to the 58% of VSV-G pseudotypes (FIG. 6), indicating a partial ablation of the virus infectivity by the polymer shell. To achieve optimal targeting transduction efficiency and minimal background infectivity, we further tested a series of combinations of different amounts of NAS and monomers (FIG. 7) with or without cRGD. We examined the transduction efficiency of the targeting nanovirus in HeLa cells. As shown in FIG. 7, transduction of nanovirus without cRGD is always lower than transduction of nanovirus with cRGD, indicating the polymer shell shielded the native infectivity of the VSV-G pseudotyped lentivirus and cRGD conferred new binding ability to the virus. In our test, we found that a combination of NAS: virus (m/m=$2\times10^4$) and monomer: virus (w/w=125) could completely shield the native viral infectivity and resulted in a transduction efficiency of 35% with cRGD, which is similar to the VSV-G pseudotypes (42%) with the same amount of p24 (FIG. 7), indicating a high infectivity of targeting nanovirus can be achieved by adjusting the gap distance and size of the polymer shell. Transduction efficiency of nanovirus without cRGD was 0% at this combinational ratio. We also determined the sizes of the nanovirus by dynamic light scattering (DLS). Size of the nanovirus ranged from ~100 nm to ~150 nm (FIG. 7). As predicted, the size of the nanovirus increased with increased amounts of monomer. The size of nanovirus with or without cRGD was similar (FIG. 7). When testing the transduction efficiency of the targeting nanovirus with the optimal ratio of NAS and monomer to virus in another RGD-expressing cell, human umbilical vein endothelial cells (HUVEC), a transduction efficiency of 8.1% was observed with a transduction efficiency of 11.7% by the VSVG pseudotypes and a transduction efficiency of 0.2% by the nanovirus without cRGD. This result suggests the possibility of using the targeting nanovirus in a variety of RGD-expressing cells.

Stability of the Targeting Nanovirus at 4° C. and Under Freeze-Thaw Cycles

VSVG pseudotyped lentivirus are stable during short time storage at 4° C. or when frozen at −70° C. and thawed. To examine whether the targeting nanovirus possess similar stability as VSVG pseudotypes, we tested the transduction by the targeting nanovirus after keeping at 4° C. for 4 h, 8 h, and 24 h as well as under freeze-thaw cycles. Experimental data showed that there were no loss of the infectivity of both VSVG pseudotypes and the targeting nanovirus at different time points, indicating the targeting nanovirus are stable at 4° C. at least for 24 hours as the VSVG pseudotypes.

When under freeze-thaw cycles, the infectivity of VSVG pseudotypes and the targeting nanovirus were stable after two cycles of freeze-thaw but reduced significantly at the third cycle of freeze-thaw, indicating the targeting nanovirus can be frozen and thawed at least twice without significantly loss of infectivity as the VSVG pseudotypes.

Transduction by Targeting Nanovirus to Hela Cells is Specifically Mediated by RGD and Integrin Interaction To confirm the specificity of the targeting transduction, we tested transduction of targeting nanovirus conjugated with a nonspecific peptide, cyclic RAD (cRAD), in Hela cells and observed no transduction, indicating the transduction of the nanovirus in Hela cells was conferred by cRGD not cRAD (FIG. 8). We also blocked HeLa cells by soluble cRGD or cRAD then transduced the cells with either VSV-G pseudotyped lentivirus or the cRGD conjugated targeting nanovirus (cRGD-nVSVG). Blocking by either cRGD or cRAD had no effect on the transduction efficiency by VSV-G pseudotyped lentivirus (FIG. 9). Blocking by cRGD but not cRAD inhibited the transduction by cRGD-nVSVG to 40% of the transduction in the absence of blocking molecules (FIG. 9). These results further support that transduction by cRGD-nVSVG in Hela cells is cRGD specific.

Integrin is the receptor for RGD peptide on cell surface. Therefore, we further tested whether the transduction by cRGD-nVSVG is integrin-dependent. We blocked the Hela cells by anti-integrin antibodies followed by transduction of VSV-G pseudoetypes or cRGD-nVSVG. Anti-integrin antibodies suppressed transduction by cRGD-nVSVG but not VSV-G pseudotypes (FIG. 9), indicating binding of cRGD on the cell surface is integrin-dependent. Isotype antibodies had no effect on either the VSV-G pseudotypes or the cRGD-nVSVG. The incomplete blocking by soluble cRGD peptide or anti-integrin antibody is probably due to the competition with the multivalent binding of the targeting nanovirus to the cell surface integrins.

Entry Kinetics of Targeting Nanovirus

Figure 10:
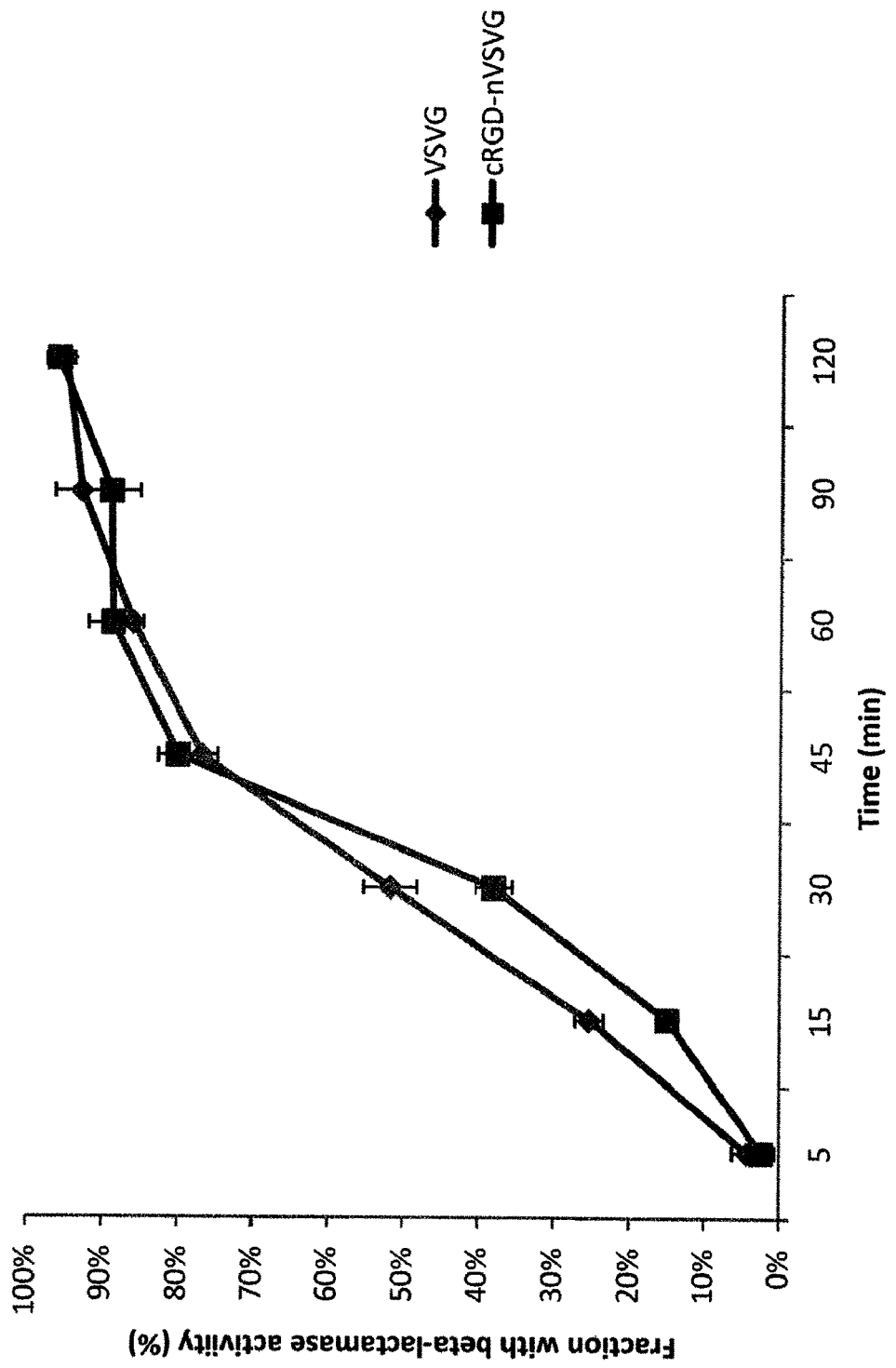
Figure 11:
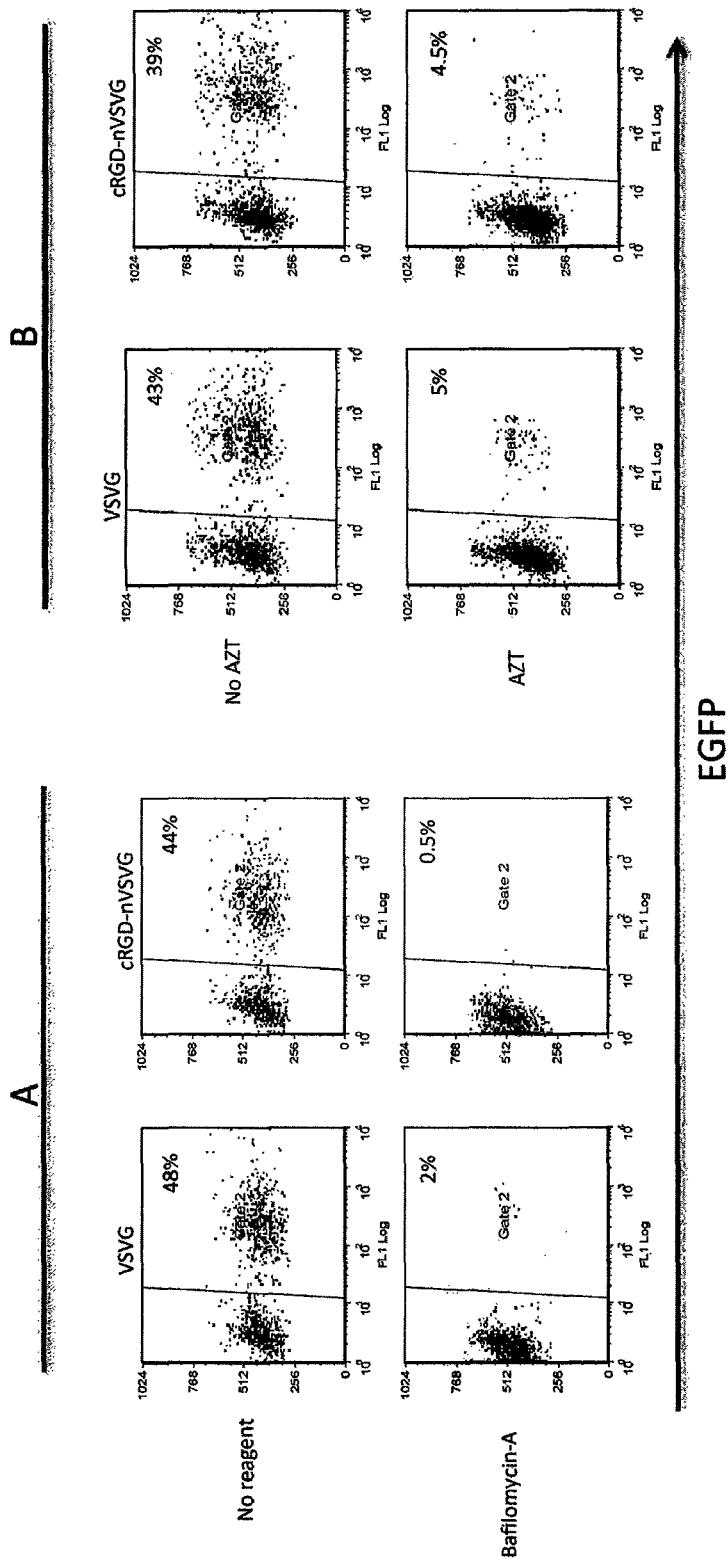
Figure 12:
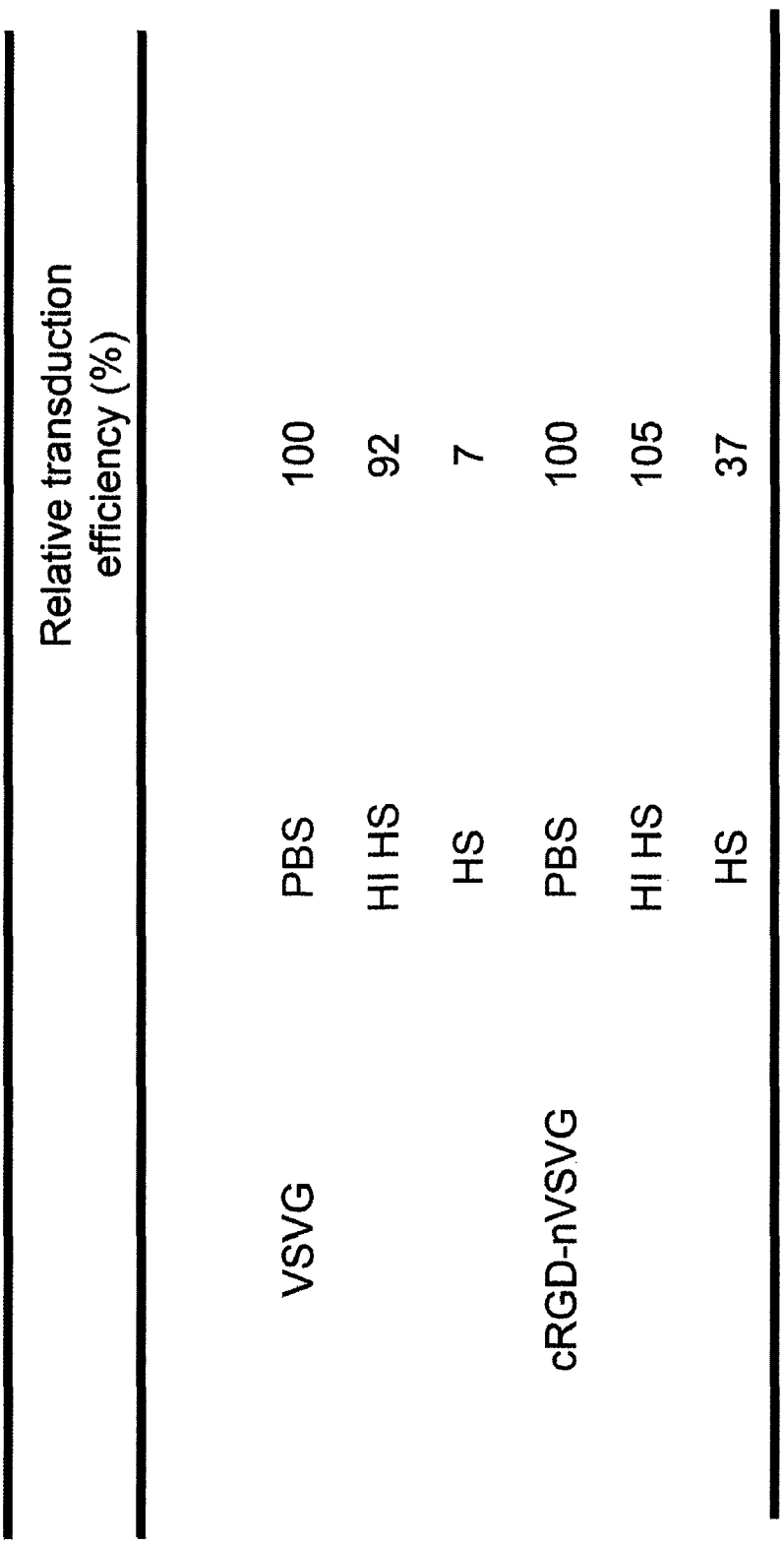

We examined the virological properties of the targeting nanovirus compared to the classical standard VSV-G pesudotypes. First, we accessed the entry kinetics of the virus by β-lactamase (BlaM) assay, which has been used previously as a measure of viral entry into cells. BlaM-Vpr fusion protein was incorporated into both VSV-G pseudotypes and targeting nanovirus. Cytosolic BlaM activity was subsequently detected by loading cells with CCF2-AM, which is converted to be a BlaM substrate by endogenous cytoplasmic esterases and retains in the cytosol. CCF2-AM exhibits a shift from green to blue fluorescence upon BlaM cleavage. BlaM activity was examined at 5, 15, 30, 45, 60, 90, and 120 minute after incubating virus with cells at 37° C. As shown in FIGS. 10, at 5, 15, and 30 minute, BlaM activity was slightly higher in VSV-G pseudotypes transduced cells compared to the targeting nanovirus transduced cells. After 30 minute incubation, no significant difference was observed for BlaM activity in both virus transduced cells (FIG. 10). These results indicated that the VSV-G pseudotypes entered cells and released BlaM slightly faster than the targeting nanovirus within the first 30 minutes. The delayed release of BlaM from the targeting nanovirus may be due to the degradation of the crosslinker thus the polymer shell before fusion of the viral membrane occurs.

Fusion of Targeting Nanovirus

Native VSV-G virus enters cells via endocytosis and fuses at the endosome. Bafilomycin-A, an inhibitor of the vacuolar-type H+-ATPase, has been used to neutralize the pH in endosome thus inhibiting pH-dependent virus fusion and the following transduction. The crosslinker of the polymer shell of the targeting nanovirus degrades at low-pH which allows release of the virion. Therefore, we hypothesized that the targeting nanovirus might also enter cells via endocytosis and the crosslinker degrades at the endosome to expose VSV-G protein for fusion. To confirm whether the endosome is the fusion site of the targeting nanovirus, VSV-G pseudotypes and targeting nanovirus were used to transduce HeLa cells with or without bafilomycin-A. In the presence of bafilomycin A, both transduction of VSV-G pseudotypes and targeting nanovirus were inhibited (FIG. 11A), indicating both virus entered and fused through the endosome and the shielding by polymer shell only ablated the binding but not fusion of the virus.

Transduction of Targeting Nanovirus can be Inhibited by Reverse Transcription Inhibitor To confirm that reverse transcription occurs during the transduction of targeting nanovirus, AZT, a reverse transcription inhibitor was used to block transduction. VSV-G pseudotypes and targeting nanovirus were used to transduce HeLa cells with or without AZT. In the absence of AZT, both virus transduced HeLa cells with transduction efficiency of 43% and 39% respectively (FIG. 11B). In the presence of AZT, both transductions were blocked (FIG. 11B), demonstrating reverse transcription is required for the infectivity by the targeting nanovirus.

Stability of the Targeting Nanovirus in the Presence of Human Serum

It has been reported that VSV-G pseudotyped HIV vectors produced in human cells can be inactivated by human serum complement, suggesting higher stability of the envelope is required for therapeutic vector in clinical applications. We further examined whether the polymer shell of the targeting nanovirus can provide a protection to the virus from the inactivation by human serum complement. VSV-G pseudotypes or targeting nanovirus were incubated with PBS, heat-inactivated human serum, or non-inactivated human serum at a 1:1 ratio for 30 minutes prior to the infection and throughout the infection. As shown in FIG. 12, after human serum treatment, transduction efficiency of VSV-G pseudotypes was reduced, which is consistent with the published data. In the presence of human serum, transduction by the targeting nanovirus was 5 fold higher compared to VSV-G pseudotypes (FIG. 12). The transduction efficiency of VSV-G pseudotypes and targeting nanovirus were similar with PBS or heat-inactivated human serum treatment. These data demonstrated that VSV-G pseudotypes can be inactivated by human serum complement and the polymer shell can protect the targeting nanovirus from inactivation by human serum.

Discussion

Successful application of gene therapy for treatment of human disease requires the efficient and safe delivery of therapeutic genes to the desired sites of expression. The most effective approach would be to develop vectors that home to and transduce specific cells and tissues. Numerous previous efforts have been made to develop retroviral vectors that can target specific cells and tissues. Typically, this involved modification of the native envelope and/or pseudotyping with other viral envelopes. These approaches have not been generally applicable because modifications in native envelope lead to large reductions in viral titer and pseudotypes with other viral envelopes are not generally applicable to targeting of many different types of cells and tissues.

We previously developed and described a targeting lentiviral vector pseudotyped with a modified version of the Sindbis virus envelope proteins that can target human leukocyte antigen (HLA) class I, CD4, CD19, CD20, CD45, CD146, CD34, P-glycoprotein of melanoma cells, and prostate stem cell antigen either in vitro or in vivo. The distinguishing properties of this vector relative to past retroviral targeting vectors were that it could be produced in high titers and home to specific cells and tissues after systemic administration via the bloodstream. However, despite our extensive analysis of the Sindbis virus envelope and genetic ablation of envelope domains that confer native binding, we still observed residual off-target infectivity in some cell types, most notably endothelial cells. We discovered that this infectivity is conferred by bovine protein S in fetal calf serum, or Gas6, its human homolog. Gas6 enhances native infectivity of pseudotypes of multiple viral envelope proteins. Gas6 mediates binding of the virus to target cells, bridging virion envelope phosphatidylserine to Axl, a TAM receptor tyrosine kinase on target cells. The interactions between native virion envelope proteins as well as between novel interactions such as those through virion phosphatidylserine let us to consider other means to ablate binding between virions and cells and to confer novel specificities.

We designed a novel nanotechnology which encapsulates the virion by a polymer shell to reduce non-specific targeting by preventing interactions between virion components and the target cells. Indeed, our results showed that the infectivity of VSV-G pseudotypes could be ablated completely by the polymer shell. For targeting delivery, we further conjugated the cRGD peptide to the polymer shell to direct targeted transduction to Hela cells. RGD specifically target $\alpha_v\beta_3$ integrin and has been considered as a ligand to deliver anti-cancer drugs to inhibit tumor angiogenesis and tumor growth. We selected the cRGD peptide, which confer greater stability and selectivity over the linear RGD, to target Hela cells as a proof of concept of the targeting delivery of the targeting nanovirus. Unlike genetic modification for desired retargeting properties, a 3-step chemical approach was used to transform a lentiviral vector into a novel targeting nanovirus; 1) anchor molecules are conjugated to the specific amino acid (lysine) of envelope proteins; 2) a thin degradable polymer network grows through in situ polymerization from those anchors; 3) the ligands (cRGD peptides) are conjugated with the polymer shell of the nanovirus to redirect binding to the desired receptor. Once internalized via endocytosis, the acid-degradable linkages of the polymer react, releasing the virion and allowing fusion and entry of the virion into the cytoplasm. This nano-engineering approach has several advantages. First, the polymer shell shields the virion envelope from interaction with cells, preventing both specific and off-target binding due to interactions between envelope proteins as well as N-glycans, and lipids, which we reported. In addition, we expect that there are as yet uncharacterized envelope-cell interactions through other carbohydrates, proteins and lipids that would contribute to off-target transduction. We optimized the polymerization of the nanovirus shell to prevent all such interactions without affecting subsequent steps involved in entry, fusion, and reverse transcription.

In addition to confer properties of targeting and reduced off-target infectivity, the targeting nanovirus also presents distinctive properties such as high titer and enhanced stability in human serum. Although VSV-G envelope possesses robust physical stability which allows it to be concentrated and achieve high titer, there are no successful attempts to transform it for targeting. Our targeting nanovirus successfully combines the advantages of both VSV-G envelope and a polymer shell to achieve targeting with high transduction efficiency and enhanced stability.

This example demonstrates the encapsulation of VSV-G pseudotyped lentivirus for efficient targeting delivery by polymer nanotechnology. This technology also allows for targeted delivery using other ligands.

CONCLUSION

This concludes the description of the preferred embodiment of the present invention. The foregoing description of one or more embodiments of the invention has been presented for the purposes of illustration and description. It is not intended to be exhaustive or to limit the invention to the precise form disclosed. Many modifications and variations are possible in light of the above teaching.

All publications, patents, and patent applications cited herein are hereby incorporated by reference in their entirety for all purposes.

What is claimed is:

1. A composition of matter comprising:
    a viral vector having an envelope and a first tissue tropism;
    a degradable polymer shell encapsulating the viral vector, wherein:
        the degradable polymer shell is formed by in situ polymerization on the viral vector envelope so as to encapsulate the viral vector;
        encapsulation of the viral vector by the degradable polymer shell decreases the first tissue tropism; and
        the degradable polymer shell is crosslinked; and
    a targeting agent coupled to the degradable polymer shell.

2. The composition of claim 1, wherein the viral vector is a Vesicular stomatitis Indiana virus G protein (VSV-G) pseudotyped lentiviral vector.

3. The composition of claim 1, wherein the cross-linked degradable polymer shell comprises N-acryloxysuccinimide (NAS), acrylamide, and glycidyl methacrylate (GMA).

4. The composition of claim 1, wherein the crosslinked polymer shell degrades in an acidic environment, thereby releasing the viral vector from the polymer shell.

5. The composition of claim 1, wherein the targeting agent is an antibody.

6. The composition of claim 1, wherein the targeting agent binds a peripheral blood mononuclear cell.

7. The composition of any one of claims 1-6, wherein the targeting agent is a cyclic arginine-glycine-aspartic acid (cRGD), said cRGB having an affinity to an $\alpha_v\beta_3$ integrin on a tumor cell.

8. The composition of claim 2, wherein the cross-linked degradable polymer shell comprises N-acryloxysuccinimide (NAS).

9. The composition of claim 2, wherein the cross-linked degradable polymer shell comprises acrylamide.

10. The composition of claim 2, wherein the targeting agent is an antibody.

11. The composition of claim 2, wherein the targeting agent binds a peripheral blood mononuclear cell.

12. A composition of matter comprising:
    a viral vector having an envelope;
    a degradable polymer shell encapsulating the viral vector, wherein:
        the viral vector exhibits a first tropism when encapsulated by the degradable polymer shell; and
        the viral vector exhibits a second tropism when the degradable polymer shell is degraded;
        the degradable polymer shell is formed on the viral vector by:
            (a) combining the viral vector with a polymerizable monomer and a crosslinking agent such that the polymerizable monomer and the crosslinking agent adsorb to surfaces of the envelope; and
            (b) polymerizing the polymerizable monomers and the crosslinking agent in situ on surfaces of the envelope so as to form a degradable polymer shell that:
                (i) is crosslinked;
                (ii) comprises a polymeric network that surrounds the envelope and that encapsulates the envelope so as to form a polymeric nanocapsule; and
    a targeting agent coupled to the degradable polymer shell.

13. The composition of claim 12, wherein the viral vector is a Vesicular stomatitis Indiana virus G protein (VSV-G) pseudotyped lentiviral vector.

14. The composition of claim 13, wherein the crosslinked polymer shell temporarily shields a native binding ability of the Vesicular stomatitis Indiana virus G protein (VSV-G) pseudotyped lentiviral vector.

15. The composition of claim 14, wherein the degradable polymer shell degrades at a pH below 6.0, thereby releasing the viral vector from the degradable polymer shell.

16. The composition of claim 15, wherein a lysine residue on the envelope is coupled to the degradable polymer shell.

17. A composition of matter comprising:
- a viral vector having an envelope and a first tissue tropism;
- a degradable polymer shell encapsulating the viral vector, wherein:
  the degradable polymer shell is formed by in situ polymerization on the viral vector envelope so as to encapsulate the viral vector and mask the first tissue tropism; and
  the degradable polymer shell is crosslinked; and
- a targeting agent coupled to the degradable polymer shell.

\* \* \* \* \*